(12) United States Patent
Reich et al.

(10) Patent No.: US 8,540,775 B2
(45) Date of Patent: Sep. 24, 2013

(54) MODULAR IMPLANT PART AND KNEE JOINT PROSTHESIS

(75) Inventors: Jan Reich, Hochemmingen (DE); Uwe Idler, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 815 days.

(21) Appl. No.: 12/156,791

(22) Filed: Jun. 3, 2008

(65) Prior Publication Data

US 2008/0306603 A1 Dec. 11, 2008

(30) Foreign Application Priority Data

Jun. 11, 2007 (DE) .......................... 10 2007 028 087

(51) Int. Cl.
*A61F 2/38* (2006.01)
(52) U.S. Cl.
USPC .................. 623/20.15; 623/20.34; 623/20.36
(58) Field of Classification Search
USPC 623/18.11, 20.14, 20.15, 20.21, 20.32–20.36, 623/23.44–23.47
See application file for complete search history.

(56) References Cited

U.S. PATENT DOCUMENTS

| 4,822,366 | A | 4/1989 | Bolesky |
|---|---|---|---|
| 4,985,037 | A | 1/1991 | Petersen |
| 5,061,271 | A | 10/1991 | Van Zile |
| 5,133,760 | A | 7/1992 | Petersen et al. |
| 5,152,796 | A | 10/1992 | Slamin |
| 5,290,313 | A | 3/1994 | Heldreth |
| 5,326,359 | A | 7/1994 | Oudard |
| 5,330,535 | A | 7/1994 | Moser et al. |
| 5,556,433 | A | 9/1996 | Gabriel et al. |
| 5,683,472 | A | 11/1997 | O'Neil et al. |
| 5,782,920 | A | 7/1998 | Colleran |
| 5,782,921 | A | 7/1998 | Colleran et al. |
| 5,824,097 | A | 10/1998 | Gabriel et al. |
| 5,879,391 | A | 3/1999 | Slamin |
| 5,944,756 | A | 8/1999 | Fischetti et al. |
| 6,063,122 | A | 5/2000 | O'Neil et al. |
| 6,071,311 | A | 6/2000 | O'Neil et al. |
| 6,086,614 | A | 7/2000 | Mumme |
| 6,126,693 | A | 10/2000 | O'Neil et al. |
| 6,146,424 | A | 11/2000 | Gray, Jr. et al. |
| 6,162,255 | A | 12/2000 | Oyola |

(Continued)

FOREIGN PATENT DOCUMENTS

| DE | 697 29 608 | 7/2005 |
|---|---|---|
| DE | 699 18 894 | 8/2005 |

(Continued)

*Primary Examiner* — Thomas J Sweet
*Assistant Examiner* — Megan Wolf
(74) *Attorney, Agent, or Firm* — Lipsitz & McAllister, LLC

(57) ABSTRACT

In order to improve a modular implant part for replacing a part of a natural knee joint with an implant component comprising a shaft extending away from the implant component and a connecting device for connecting the shaft to the implant component such that the shaft is adapted to be fixed to the implant component in a multiplicity of desired positions in a simple manner, it is proposed that the connecting device be formed in such a manner that, in a mounting disposition, the shaft is adapted to be moved into different translatory positions by a translatory movement in a direction transverse or substantially transverse to its longitudinal axis, and that, in an implantation disposition, the shaft is adapted to be fixed immovably to the implant component in one of the different translatory positions. Furthermore, an improved knee joint prosthesis is proposed.

27 Claims, 12 Drawing Sheets

(56) References Cited

U.S. PATENT DOCUMENTS

| | | |
|---|---|---|
| 6,171,342 B1 | 1/2001 | O'Neil et al. |
| 6,214,052 B1 | 4/2001 | Burkinshaw |
| 6,423,096 B1 | 7/2002 | Musset et al. |
| 6,436,145 B1 | 8/2002 | Miller |
| 6,506,216 B1 * | 1/2003 | McCue et al. ............. 623/20.34 |
| 6,527,807 B1 | 3/2003 | O'Neil et al. |
| 6,620,168 B1 | 9/2003 | Lombardo et al. |
| 6,699,290 B1 | 3/2004 | Wack et al. |
| 6,869,447 B2 | 3/2005 | Lee et al. |
| 6,923,832 B1 | 8/2005 | Sharkey et al. |
| 6,953,479 B2 | 10/2005 | Carson et al. |
| 7,025,788 B2 | 4/2006 | Metzger et al. |
| 7,153,326 B1 | 12/2006 | Metzger |
| 2002/0120340 A1 | 8/2002 | Metzger et al. |
| 2002/0120341 A1 | 8/2002 | Stumpo et al. |
| 2003/0014120 A1 | 1/2003 | Carson et al. |
| 2003/0055508 A1 | 3/2003 | Metzger et al. |
| 2003/0055509 A1 | 3/2003 | McCue et al. |
| 2003/0204264 A1 | 10/2003 | Stumpo et al. |
| 2004/0049286 A1 | 3/2004 | German et al. |
| 2005/0154470 A1 | 7/2005 | Sekel |
| 2006/0030945 A1 | 2/2006 | Wright |

FOREIGN PATENT DOCUMENTS

| | | |
|---|---|---|
| EP | 0 502 815 | 9/1992 |
| EP | 0 376 658 | 6/1994 |
| EP | 0 545 833 | 4/1997 |
| EP | 0 947 181 | 10/1999 |
| EP | 0 980 679 | 2/2000 |
| EP | 0 985 386 | 3/2000 |
| EP | 0 986 994 | 3/2000 |
| EP | 0 993 813 | 4/2000 |
| EP | 0 714 645 | 5/2000 |
| EP | 0 853 930 | 7/2002 |
| EP | 1 234 557 | 8/2002 |
| EP | 0 781 535 | 5/2003 |
| EP | 0 820 739 | 6/2004 |
| EP | 0 956 836 | 7/2004 |
| EP | 0 966 928 | 9/2005 |
| EP | 1 623 686 | 2/2006 |
| WO | 03/007852 | 1/2003 |
| WO | 03/065939 | 8/2003 |
| WO | 2007/114841 | 10/2007 |

* cited by examiner

MODULAR IMPLANT PART AND KNEE JOINT PROSTHESIS

The present disclosure relates to the subject matter disclosed in German patent application No. 10 2007 028 087.6 of Jun. 11, 2007 which is incorporated herein by reference in its entirety and for all purposes.

BACKGROUND OF THE INVENTION

The present invention relates to a modular implant part for replacing a part of a natural knee joint with an implant component comprising a shaft extending away from the implant component and a connecting device for connecting the shaft to the implant component.

Furthermore, the present invention relates to a knee joint prosthesis comprising a first implant part in the form of a femoral part, a second implant part in the form of a tibial part and a third implant part in the form of a meniscus part, wherein the first and/or the second implant part is a modular implant part for replacing a part of a natural knee joint with an implant component comprising a shaft extending away from the implant component and a connecting device for connecting the shaft to the implant component.

Modular implant parts of the type described hereinabove are used in order to obtain particularly stable embedding of the implant in the bone. For this purpose, shafts in the form of extension shafts are used and they are inserted into a medullary cavity of a partially resected bone, for example, the femur or the tibia of a patient so as to enable the shafts and hence the implant part to be better supported on the bone. The shafts for the respective implant part are usually available in different lengths and angles. Moreover, in order to enable the position of the shaft relative to the implant component to be ideally matched to the anatomy of a patient, it is advantageous if the shafts are adapted to be mounted on the implant component in different positions.

Examples of modular implant parts of this type are known from U.S. Pat. No. 5,782,920, US 2003/0055508 A1 and U.S. Pat. No. 5,290,313. The disadvantage of the implant parts described in the aforesaid documents is, however, that the shaft can only be mounted on the implant component at defined angular positions or with a defined lateral displacement using appropriate adapters so that, in turn, a multiplicity of appropriate adapters is necessary for different positions of the shaft.

Consequently, it would be desirable to provide a modular implant part and a knee joint prosthesis of the type described hereinabove which would allow fixing the shaft the implant component at a multiplicity of desired positions in a simple manner.

SUMMARY OF THE INVENTION

In accordance with the invention, it is suggested in the case of a modular implant part of the type described hereinabove that, in a mounting disposition, the connecting device is formed in such a manner that the shaft is adapted to be moved into different translatory positions by a translatory movement in a direction transverse or substantially transverse to its longitudinal axis and that, in an implantation disposition, the shaft is adapted to be fixed immovably to the implant component in one of the different translatory positions.

An improved modular implant part of this type enables one to manage without a multiplicity of adapters or shafts in order to connect the implant component to a shaft and implant it in the most varied of implantation dispositions. Due to the translatory movements in a direction transverse or substantially transverse to the longitudinal axis of the shaft that are made possible by means of the connecting device, a lateral displacement of the shaft on the implant component can be established in the desired manner. Different adapters or different shafts for the purposes of mounting on the implant component in differing positions are therefore superfluous. This reduces the manufacturing complexity and thus the costs of the modular implant part on the one hand, whilst increasing the facility of observing the process in an operating theatre on the other, because the operating surgeon can match the modular implant part directly to the anatomy of the respective patient. Thus, in particular, optimal coverage of a partially resected bone by the implant component can be ensured in a simple and safe manner.

Advantageously, the connecting device is formed in such a manner that it is possible for different translatory positions to be set in step-less manner in the mounting disposition. Thus, the modular implant part can be adapted to the anatomy of a patient in an optimal and step-less manner.

It is expedient, if, in the mounting disposition, the shaft is rotatable about an axis of rotation, which runs parallel or substantially parallel to the longitudinal axis of the shaft, into different rotary positions relative to the implant component. This arrangement enables the shaft to be positioned on the implant component practically at will because it can be moved into different translatory positions and rotated into different rotary positions, whereby any arbitrary superimposition of the translatory and rotary movements of the shaft relative to the implant component is possible.

In order to enable the shaft to be fixed to the implant component in the implantation disposition in a durable and secure manner, it is expedient if, in the implantation disposition, the shaft is adapted to be fixed immovably to the implant component by the connecting device in one of the different rotary positions. In particular, the connecting device can also be formed in such a manner that it is possible to fix the translatory position and the rotary position independently of each other. In particular, this permits a desired translatory position to be firstly set and fixed and then subsequently, for the shaft to be moved into a desired rotary position. It is self-evident that the reverse procedure is also conceivable.

In principle, it would be conceivable to form the implant part in such a manner that the shaft is adapted to be fixed to the implant component in only certain defined rotary positions. Advantageously however, the connecting device is formed in such a manner that it is possible to set-up differing rotary positions in step-less manner in the mounting disposition. In this manner, an operating surgeon is not subjected to any restriction in regard to the adjustment of the modular implant part. He can therefore match it individually and optimally to the anatomy of the patient.

In order to enable the shaft to be connected to the implant component in a simple manner, it is expedient if the connecting device comprises at least one adapter which, in the mounting disposition, is adapted to be fixed to the implant component on the one hand and to the shaft on the other. This permits the modular implant part to be formed with a minimum number of parts.

The structure of the modular implant part can be further simplified if the at least one adapter comprises an adapter element which is symmetrically or substantially symmetrically formed. This additionally simplifies the production process and reduces the costs of the implant part.

In order to enable the implant component to be connected to the adapter in a simple manner, it is advantageous for the implant component to comprise a first coupling member which is in engagement with the adapter in force-locking and/or shape-locking manner in the implantation disposition. In particular, the stability of the implant part can thereby be established in the desired manner.

Preferably, the first coupling member is constructed in the form of a coupling projection. For example, the shaft can be fixed directly to the coupling projection with or without an adapter. In addition, the coupling projection can, for example, engage in a simple manner with a corresponding coupling seating in the implantation disposition, this thereby permitting particularly good support of the shaft on the implant component.

It is advantageous if the connecting device comprises a first coupling device for immovably fixing the at least one adapter to the implant component in the implantation disposition. With the aid of such a coupling device, the adapter, and via it the shaft too, can be fixed to the implant component in a simple and secure manner.

A particularly simple construction of the first coupling device can be achieved in that the first coupling device comprises at least two first coupling elements which are in engagement in the implantation disposition, and in that the implant component comprises one of the at least two first coupling elements and in that the adapter comprises another of the at least two first coupling elements.

The modular implant part can be constructed in a particularly compact manner if the first coupling member comprises one of the at least two first coupling elements.

The adapter and the implant component can be interconnected in a secure and durable manner if one of the at least two first coupling elements comprises an internally threaded section and another of the at least two first coupling elements comprises a corresponding externally threaded section. The two parts that are to be interconnected can thus be screwed together in a simple manner.

Advantageously, one of the at least two first coupling elements comprises a recess and another of the at least two first coupling elements comprises a projection which enters the recess in the implantation disposition. Thus, in particular, a temporary connection can be established between the parts that are to connected together in the mounting disposition, but nevertheless a relative movement therebetween is still possible.

The construction of the coupling device is particularly simple if the recess is in the form of a groove and the projection is in the form of a screw, whereby at least one part of the screw enters the groove in the implantation disposition. Thus, in particular, the implant part can be transferred from the mounting disposition into the release position and/or vice versa by a simple movement of the screw.

In order to keep the number of necessary parts of the modular implant part as small as possible, it is expedient if the adapter and the first coupling element comprised thereby are formed in one piece. Furthermore, the stability of the implant part can also be increased thereby.

In order to enable a particularly secure connection between the adapter or the shaft and the implant component to be established, it is expedient if the first coupling device comprises a first fastening element, if the first fastening element comprises the at least one first coupling element of the adapter and if, in the implantation disposition, the first fastening element is supported on the adapter on the one hand and is connected to the implant component on the other hand, or vice versa. In particular, such an arrangement enables the adapter to be applied to the implant component from one side without the need to provide a through opening in the implant component. For example, the first fastening element can be in the form of a screw having a threaded section which passes through a through opening in the adapter, a head which is supported on the adapter, and the threaded section thereof being adapted to be screwed to the implant component.

Furthermore, in accordance with a preferred embodiment of the invention, provision may be made for the connecting device to comprise a second coupling device for immovably fixing the at least one adapter to the shaft in the implantation disposition. Accordingly, the adapter can be fixed to the shaft with the aid of the second coupling device. Preferably, in different positions.

It is advantageous if the second coupling device comprises at least two second coupling elements which are in engagement in the implantation disposition, and if the shaft comprises one of the at least two second coupling elements, and if the adapter comprises another one of the at least two second coupling elements. In particular, the two second coupling elements can be formed in such a manner that the shaft and the adapter are adapted to be fixed relative to one another in mutually different translatory positions in the implantation disposition.

The construction of the implant part is particularly simple if the shaft comprises a second coupling member which is in engagement with the adapter in force-locking and/or shape-locking manner in the implantation disposition. In particular, the shaft and the adapter can engage with one another in different translatory positions and/or rotary positions in the implantation disposition.

In order to construct the implant part in a yet more compact manner, it is advantageous if the second coupling member comprises one of the at least two second coupling elements.

The manufacture of the implant part is particularly simple if the second coupling member is constructed in the form of a coupling projection. It is self-evident that it could also be constructed in the form of a coupling seating.

In order to enable the adapter and the shaft to be interconnected in a simple manner and in particular, to enable them to be screwed together, it is advantageous if one of the at least two second coupling elements comprises an internally threaded section and if another one of the at least two second coupling elements comprises a corresponding externally threaded section. In addition, threaded sections are simple and economical to manufacture.

Moreover, it can be expedient if one of the at least two second coupling elements comprises a recess and if another one of the at least two second coupling elements comprises a projection which enters the recess in the implantation disposition. Thus in particular thereby, a positive connection between the two second coupling elements can be established in a simple manner.

Preferably, the recess is in the form of a groove and the projection is in the form of a screw, whereby at least one part of the screw enters the groove in the implantation disposition. In particular, this arrangement further simplifies the construction of the modular implant part.

The number of parts necessary for the construction of the modular implant part can be further reduced if the adapter and the second coupling element comprised thereby are formed in one piece.

In order to achieve simple attachment of the adapter to the shaft, it is expedient if the second coupling device comprises a second fastening element which connects the adapter to the shaft in the implantation disposition.

A particularly compact construction of the modular implant part can be achieved if the second fastening element comprises the at least one second coupling element of the adapter and if, in the implantation disposition, the second fastening element is supported on the adapter on the one hand and is connected to the shaft on the other. In particular, such an arrangement enables a screw to be envisaged as the second fastening element, the head thereof being supported on the adapter and the threaded section thereof being adapted to be screwed to the shaft.

It is advantageous if the connecting device comprises a first guidance device for guiding a movement of the adapter and the implant component relative to each other in the mounting disposition. The guidance device enables the shaft to be transferred relative to the implant component in a defined manner from one translatory position into another translatory position and/or from one rotary position into another rotary position.

It is particularly advantageous if the first guidance device comprises a rotary guide means. The shaft and the implant component can thereby be rotated relative to each other in a defined manner.

The construction of the implant part is particularly compact if the first guidance device comprises the first coupling member. The number of necessary parts in the implant part can thereby be minimized.

Furthermore, in accordance with a preferred embodiment of the invention, provision may be made for the connecting device to comprise a second guidance device for guiding a movement of the adapter and the shaft relative to each other in the mounting disposition. Thus, in particular thereby, the shaft can be moved relative to the adapter and hence the shaft relative to the implant component in a defined manner.

The construction of the implant part is particularly simple if the second guidance device comprises a linear guide means. With the aid of such a linear guide means, it is possible to set a defined displacement of the shaft and the implant component relative to each other in a simple manner.

It is advantageous, if the second guidance device comprises at least one guide groove formed on the adapter and/or on the shaft and if the second coupling member is guided in the guide groove in movable manner in the mounting disposition. Formation of a guide groove is technically simple from both a constructional and manufacturing point of view and enables defined and stable guidance of the shaft and the adapter relative to each other to be obtained. In particular, the guide groove can be in the form of a straight-line or curved.

Expediently, the second guidance device comprises the second coupling member. In this manner, the number of components needed for the production of the modular implant part can be further reduced.

As already stated above, it is expedient, if the shaft and the implant component can be adjusted relative to each other in step-less manner. However, it can also be expedient if provision is made for a positioning device for positioning the shaft and the implant component relative to each other in a plurality of discrete positions. In particular, the stability of the modular implant part can be thereby increased. Furthermore, it is also simpler for some operating surgeons if a translatory position or a rotary position can be selected from a plurality of discrete positions in order to match the modular implant part to the anatomy of the patient.

Advantageously, the positioning device comprises a rotary positioning device for positioning the shaft and the implant component relative to each other in a plurality of discrete rotary positions. Thus, certain specific relative angular positions of the shaft and the implant component can be predefined by the manufacturer by appropriate construction of the rotary positioning device. In particular, relative positions which would not be desired at all in practice can also be completely excluded thereby.

Preferably, the positioning device comprises a linear positioning device for positioning the shaft and the implant component relative to each other in a plurality of discrete translatory positions. Here too, desirable frequently occurring translatory positions can be predefined for an operating surgeon in order to position the shaft and the implant component relative to each other in a defined manner. Self-evidently, the positioning device can be formed in such a manner that the linear positioning device and the rotary positioning device are effective and can be used mutually independently. This means, in particular, that a translatory position can be altered prior to, during or after a change of a rotary position.

The construction of the positioning device is particularly simple if it comprises at least two sets of teeth which are in engagement in the implantation disposition and if sets of teeth are provided on the implant component and on the adapter and/or on the adapter and on the shaft. Sets of teeth are simple to manufacture and are best suited to establishing defined translatory or rotary positions.

Advantageously, the sets of teeth are in the form of toothed rings and/or in the form of linear sets of teeth. Toothed rings are excellently suited to the formation of rotary positioning devices, linear sets of teeth are excellent for the formation of linear positioning devices. The sets of teeth can be formed such that they are oriented in each case in the direction of the parts of the implant part that fit together or else transverse thereto. In particular, rows of tooth can be provided with teeth which extend in parallel with a longitudinal axis of the shaft or which extend perpendicularly thereto.

Expediently, there is provided at least one securing device for securing the first and/or second coupling device in the implantation disposition. The connection of the shaft to the implant component is additionally improved by the securing device, whereby a direct or indirect connection to the securing device is possible.

The construction of the securing device is particularly simple if it comprises a lock nut. Thus, in particular, parts that are screwed to one another can be secured in a connecting position, in the implantation disposition for example.

In order to prevent the medullary cavity of a bone being damaged or in order to minimize the risk thereof by the insertion of the shaft, it is advantageous if a plurality of shafts of different lengths are provided. In particular thereby, an implant-set can also be formed which comprises a modular implant part and a multiplicity of shafts of different lengths and/or different shapes, for example, of different curvature and different diameters.

In accordance with a preferred embodiment of the invention, provision can be made for the implant component to comprise artificial femoral condyles between which a depression is formed. In particular, a femoral part of a knee joint prosthesis can be formed with the aid of an implant component of this type. Preferably, the implant part forms a femoral part of a knee joint prosthesis. In particular thereby, a part of the femur which forms the natural condyles can be optimally replaced.

Furthermore, it can be expedient if the implant part forms a tibial part of a knee joint prosthesis. Such an implant part can be optimally matched to the anatomy of the part of the tibia on the knee joint side.

In order to enable a meniscus part to be supported on a knee joint prosthesis in a simple and secure manner, it is expedient if the implant component comprises a plate-like tibia plateau. In particular, a meniscus part can be placed flat upon the tibia plateau and moved relative thereto.

Furthermore, in accordance with the invention, it is suggested in the case of a knee joint prosthesis of the type described hereinabove that the connecting device is formed in such a manner that, in a mounting disposition, the shaft is adapted to be moved into different translatory positions by a translatory movement in a direction transverse or substantially transverse to its longitudinal axis and that, in an implantation disposition, the shaft is adapted to be fixed immovably to the implant component in one of the different translatory positions.

Such a knee joint prosthesis can be matched in an optimal manner to the anatomy of a patient. In particular, it can be designed in such a manner that the implant component ensures maximum coverage of a partially resected bone end.

Furthermore, it is expedient if the first and/or the second implant part is one of the modular implant parts described above. Such an implant part then has the advantages mentioned above in connection with the embodiments described.

The following description of preferred embodiments of the invention serves for a more detailed explanation taken in conjunction with the drawing. Therein:

DETAILED DESCRIPTION OF THE INVENTION

Figure 1:
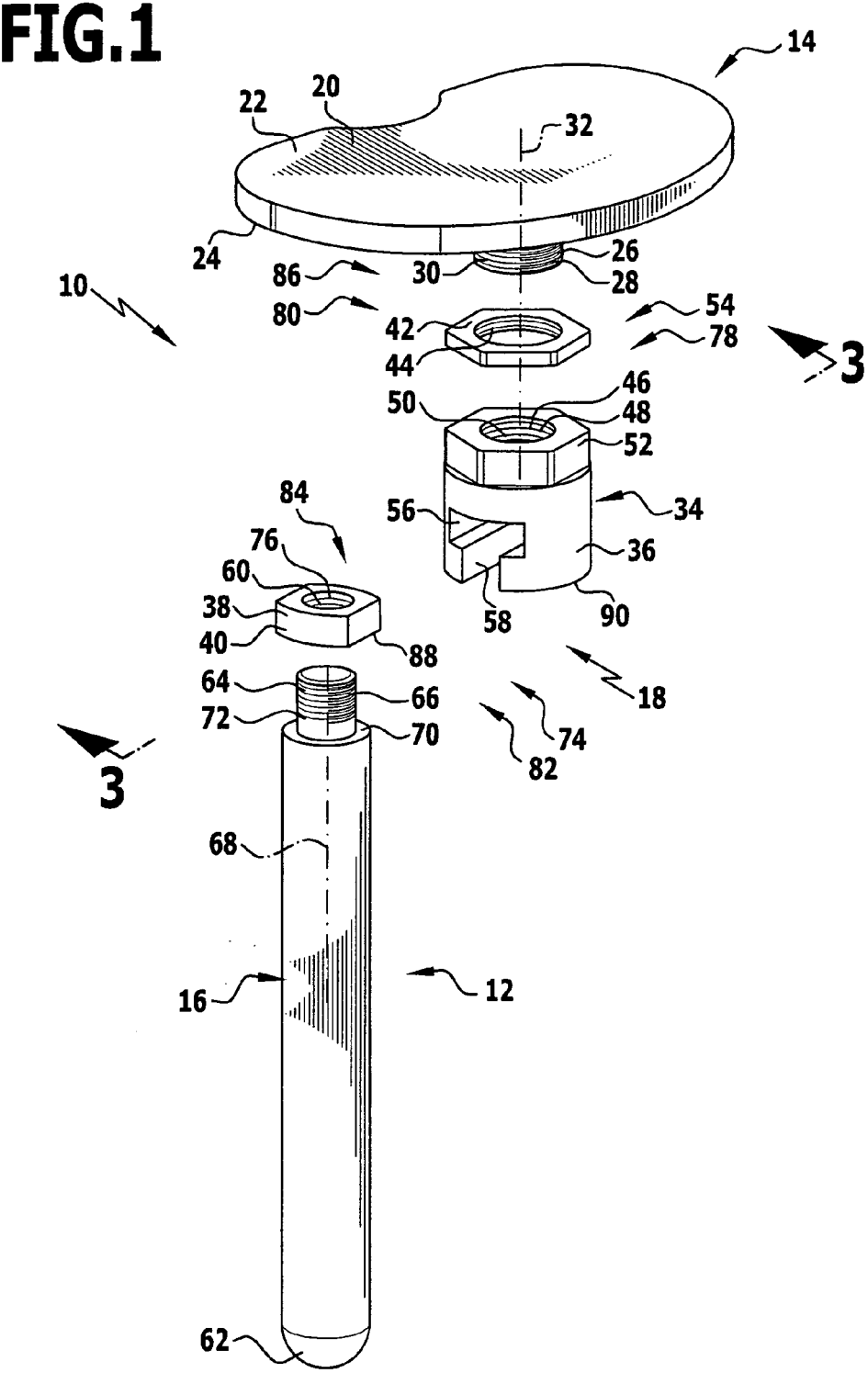
FIG. 1: shows an exploded view of a first exemplary embodiment of a modular implant part.
Figure 2:
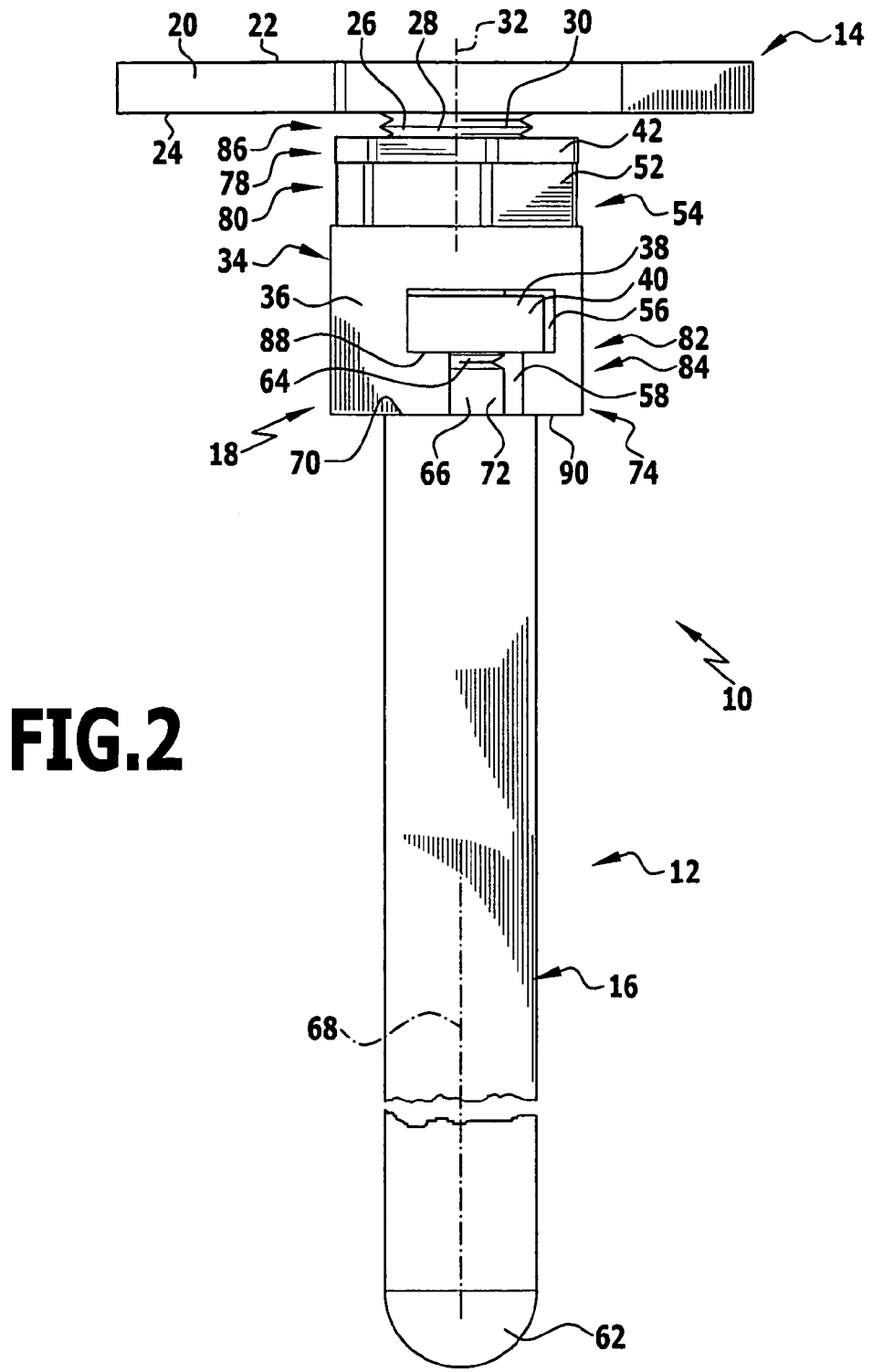
FIG. 2: a side view of the implant part depicted in FIG. 1 in an implantation disposition.
Figure 3:
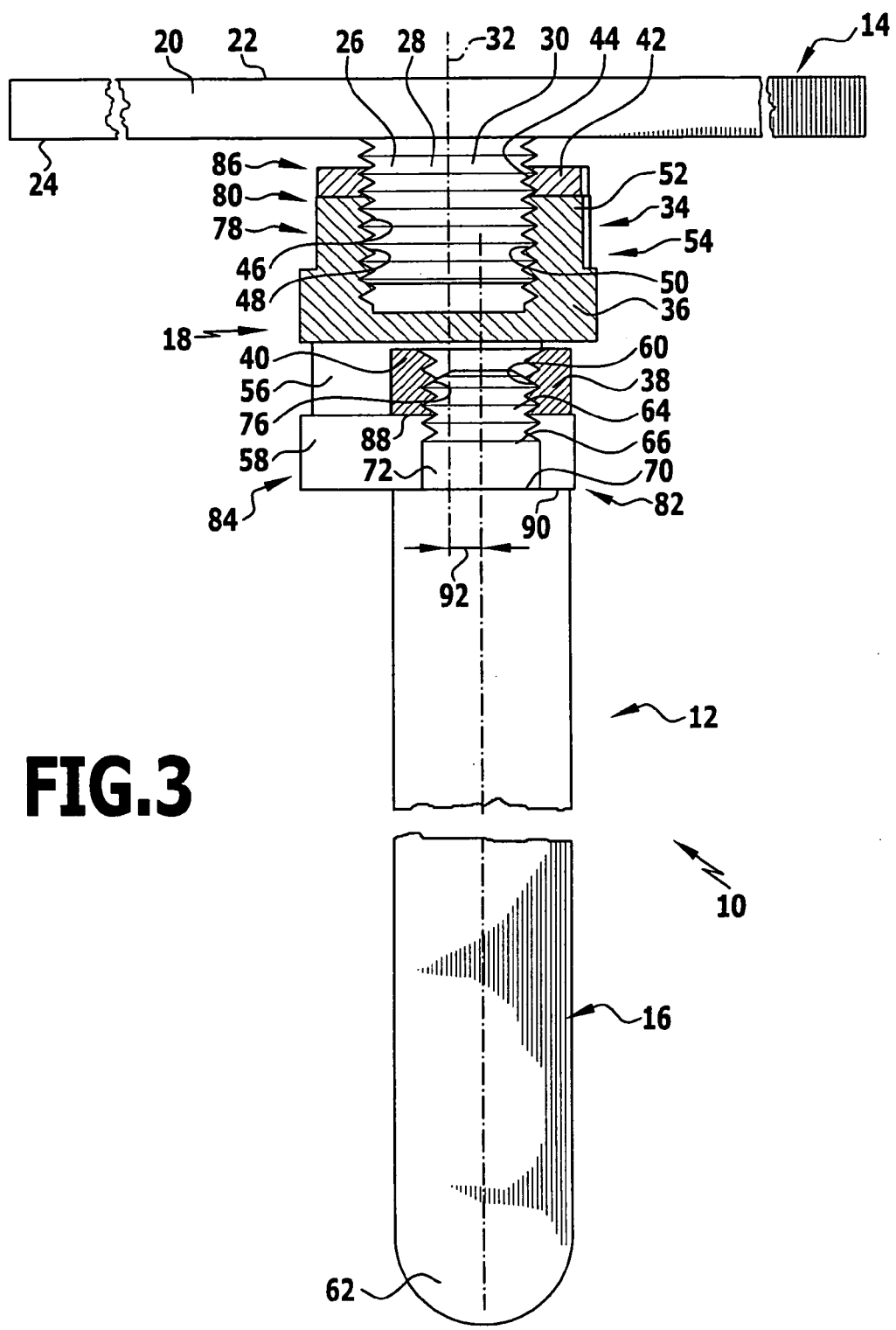
FIG. 3: a sectional view of the implant part depicted in FIG. 2 along the line 3-3 in FIG. 1 in the implantation disposition.

A first exemplary embodiment of a modular implant part is provided with the general reference symbol 10 in FIGS. 1 to 3. It is illustrated in the form of a tibial part 12 of a knee joint prosthesis which, furthermore, comprises a femoral part and optionally too, a likewise not illustrated meniscus part.

The implant part 10 comprises an implant component 14, an elongated, round rod-shaped shaft 16 as well as a connecting device 18 for connecting the implant component 14 to the shaft 16.

The implant component 14 comprises a plate which is substantially kidney-shaped in a top view and forms a tibia plateau 20 the upper surface 22 and lower surface 24 of which are completely flat in the exemplary embodiment illustrated in the Figures. A coupling member 26 in the form of a stud-like projection 28 extends centrally away from the middle of the lower surface 24, this member being provided with an external thread 30 over its entire length. The coupling member 26 is connected in one piece manner to the implant component 14 and thus in toto forms a threaded bolt which defines a longitudinal axis 32.

The connecting device 18 comprises an adapter 34 which, in turn, comprises an adapter element 36 that is mirror-symmetrical relative to a mirror plane containing the longitudinal axis 32, a coupling element 38 in the form of a slide block 40 and a lock nut 42. The lock nut 42 has an internal thread 44 which is formed so as to correspond to the external thread 30. In the cross section transverse to the longitudinal axis 32, the lock nut 42 has a hexagonal outer contour.

An upper portion of the adapter element 36 comprises a further coupling element 46 in the form of an internally threaded section 48 of a blind hole 50 which is formed such as to be coaxial with the longitudinal axis 32. An upper end 52 of the adapter element 36 is thus in the form of a hexagon nut whose height corresponds to about a quarter of the overall length of the adapter element 36 parallel to the longitudinal axis 32. The coupling elements 38 and 46 form first coupling elements of a first coupling device 54 for the purposes of fixing the adapter 34 to the implant component 14.

The lower half of the adapter element 36 has a T-shaped guide groove 56 which is oriented transversely relative to the longitudinal axis 32 and is formed by two cuboidal through openings which are oriented perpendicularly to each other. The adapter element 36 is downwardly open by virtue of a slot 58 which forms a part of the guide groove 56 and is, in effect, the perpendicular stroke of the "T". In addition, the guide groove 56 is formed in such a manner that the cuboidal slide block 40, which is provided with an internally threaded boring 60, can be shifted transversely relative to the longitudinal axis 32 in a section of the guide groove 56 which quasi forms the cross-stroke of the "T".

The distal end 62 of the shaft is rounded off in hemispherical manner. The proximal end of the shaft comprises a second coupling member 64 in the form of a threaded bolt 66 which is coaxial with respect to a longitudinal axis 68 of the shaft 16 whilst the outer diameter thereof is somewhat reduced with respect to the shaft 16. This thus results in a ring-like surface 70 that faces in the proximal direction and is oriented transversely of the longitudinal axis 68. The threaded bolt 66 comprises a second coupling element 72 in the form of an external thread which is formed such as to correspond to an internal thread of the internally threaded boring 60. The slot 58 is of such a width that the threaded bolt 66 can be introduced therethrough coming from the distal end, i.e. in a direction towards the implant component 14, and it can also be displaced in the slot 58 transversely relative to the longitudinal axis 68. The connecting device 18 thus comprises not only the first coupling device 54, but also a second coupling device 74 which comprises the second coupling member 64 as well as the second coupling element 72 and the internally threaded boring 60 of the slide block 40 likewise forming a second coupling element 76.

As will be explained in more detail hereinafter, the implant part 10 comprises a first guidance device 78 in the form of a rotary guide means 80 for guiding rotational movement of the adapter 34 and the implant component 14 relative to each other. It comprises, in particular, the first coupling member 26. Furthermore, there is provided a second guidance device 82 for guiding movement of the adapter 34 and the shaft 16 relative to each other, this being in the form of a linear guide means 84. Moreover, there is provided a securing device 86 which comprises the lock nut 42 for securing a connection of the first coupling device 54 in an implantation disposition in which all the parts of the implant part 10 are firmly connected to one another.

The, in all, five parts of the implant part 10 are assembled as follows. Firstly, the lock nut 42 is screwed onto the first coupling member 26. Then, the adapter element 36 is likewise screwed onto the coupling member 26. The rotary guide means 80 comprising the first coupling member 26 and the internally threaded section 58 of the blind hole 50 enables arbitrary alignment of the adapter element 36 about the longitudinal axis 32, i.e. the guide groove 56 can be adjusted into any rotary position with respect to the longitudinal axis 32. As long as the lock nut 42 is not tightened up against the end 52 of the adapter element 36, the implant part 10 adopts a so-called mounting disposition in which another relative movement of the adapter element 36 and the implant component 14 is still possible.

Moreover, the second coupling member 64 is screwed into the slide block 40, namely, in such a manner that the spacing between a lower surface 88 and the ring-shaped surface 70 is greater than the height of the slot 58 parallel to the longitudinal axis 68. The slide block 40 together with the shaft 16 screwed therein can then be slid transversely relative to the longitudinal axis 68 into the guide groove 56, whereby the threaded bolt 66 passes through the slot 58. The linear guide means 84 comprising the slide block 40 and the guide groove 56 enables step-less adjustment of the shaft 16 and the adapter element 36 relative to each other in the mounting disposition, in which they are not as yet firmly connected together. Should the slide block 40 and the coupling member 64 be screwed firmly together, the ring-shaped surface 70 presses against a distal end face 90 of the adapter element 36 running transversely relative to the longitudinal axis 68 so that the shaft 16 is held clamped onto the adapter 34 in the implantation disposition.

When the implant part 10 is adjusted in the desired manner, i.e. a relative position of the shaft 16 and the adapter 34 as well as a desired rotary position of the adapter 34 relative to the implant component 14, the first and second coupling device 54 and 74 can be transferred from the mounting disposition into the implantation disposition, namely as already described above for the second coupling device, by screwing the shaft 16 into the slide block 40 and also by mutually tightening the lock nut 42 against the end 52 of the adapter element 36. Due to the second guidance device 82 comprised by the connecting device 18, the shaft 16 can, in the mounting disposition, be moved in step-less manner into different translatory positions by means of a translatory movement in a direction transverse to the longitudinal axis 68, such positions defining a lateral displacement 92, i.e. a spacing between the longitudinal axes 32 and 68. Thus, in toto, the shaft 16 can be fixed immovably to the implant component 14 in any rotary position about the longitudinal axis 32 and with any arbitrary displacement 92 relative thereto.

Figure 4:
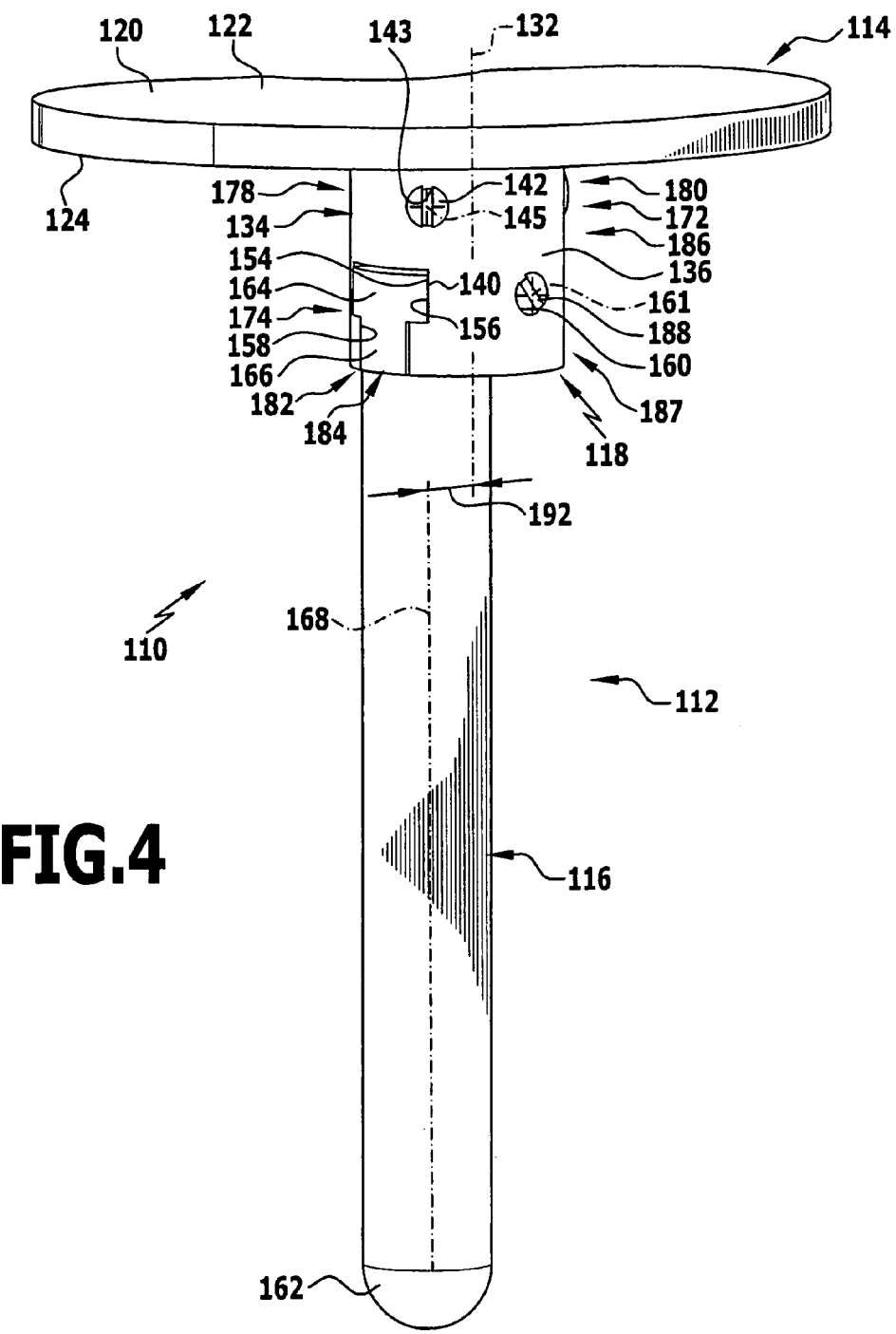
FIG. 4: a perspective view of a second exemplary embodiment of a modular implant part.
Figure 5:
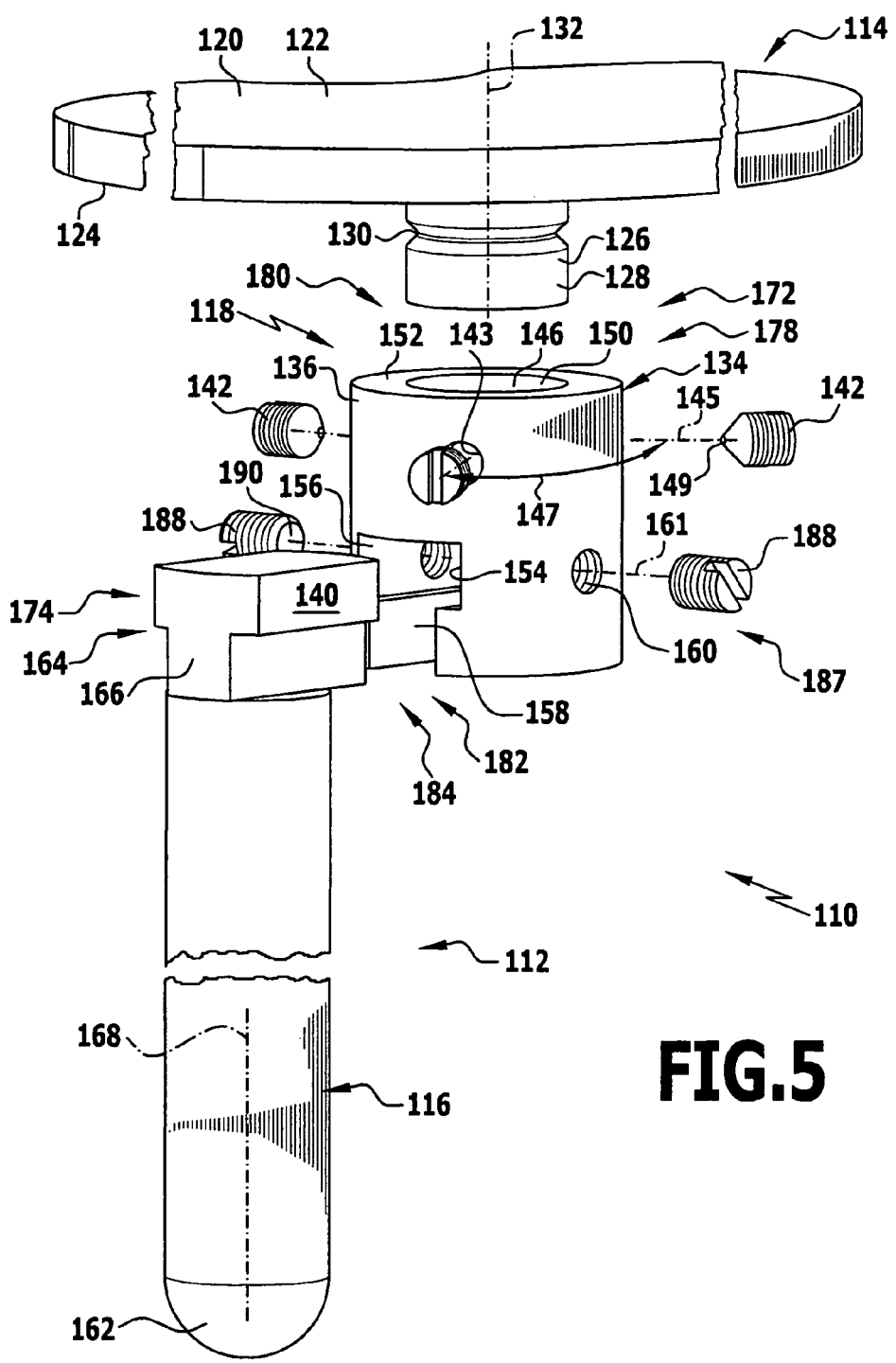
FIG. 5: an exploded view of the implant part depicted in FIG. 4.

A second exemplary embodiment of an implant part provided with the general reference symbol 110 is illustrated in FIGS. 4 and 5. It differs from the implant part 10 by virtue of the construction of the connecting device 118. Consequently, for the sake of clarity hereinafter, the parts of the implant part 110 which correspond to parts of the implant part 10 are provided with reference symbols which exhibit the same two end digits as the reference symbols used for identifying the parts of the implant part 10.

The implant part 110 likewise forms a tibial part 112 having a plate-like implant component 114. From a lower surface 124 thereof, there protrudes a first coupling member 126 in the form of a cylindrical projection 128 which defines a longitudinal axis 132. Moreover, a peripheral annular groove 130 having a wedge-shaped profile is formed in the projection 128.

Furthermore, the implant part 110 comprises a shaft 116 as well as a connecting device 118 for connecting the implant component 114 to the shaft 116.

An adapter 134 of the connecting device 118 comprises an adapter element 136 which is very similar in terms of its fundamental construction to the adapter element 36. It takes the form of a cylindrical section and is formed symmetrically relative to a plane of symmetry containing the longitudinal axis 132. The upper or proximal-side end 152 of the adapter element 136 has a blind hole 150 which is open in the proximal direction and is formed coaxially relative to the longitudinal axis 132, it also forming a coupling element 146 of a first coupling device 154. Furthermore, the latter also comprises the coupling member 126. The coupling member 126 is adapted to be inserted into the blind hole 150 in positive manner so that the adapter element 136 is rotatable relative to the implant component 114.

For the purposes of securing a connection between the adapter 134 and the implant component 114 in the implantation disposition in which all the parts of the implant part 110 are firmly connected together, there is provided a securing device 186. It comprises three set-screws 142 which are formed such as to correspond to three threaded borings 143 the longitudinal axes 145 of which define a plane extending perpendicularly to the longitudinal axis 132, are mutually displaced by a respective angle 147 of 120° and pass through a wall of the adapter element 136 surrounding the blind hole 150. Each of the set-screws 142 has a conical point 149 which can engage in the annular groove 130 when the set-screw 142 is screwed into the respective threaded boring 143. As long as the set-screws 142 only engage in the annular groove 130, but not however such that their points 149 press against it, the adapter element 136 can be rotated relative to the implant component 114. Thus, the implant part 110 also comprises a first guidance device 178 in the form of a rotary guide means 180 which comprises the coupling member 126 and the blind hole 150.

The lower end of the adapter element 136 has a guide groove 156 which is T-shaped in longitudinal section and has an open slot 158 oriented in the distal direction. In the vicinity of the guide groove 156, in which the slide block 40 was guided in the case of the guide groove 56, there are formed two threaded borings 160 the longitudinal axes 161 of which are aligned coaxially of each other, whereby the longitudinal axes 161 intersect the longitudinal axis 132 perpendicularly. Furthermore, the longitudinal axes 161 are oriented perpendicularly relative to a plane defined by the slot 158.

The shaft 116 has a distal end 162 which is rounded off in hemispherical manner. At the proximal end of the elongated, round rod-shaped shaft 116, there is formed a second coupling member 164 which is in the form of a projection 166 that is T-shaped in longitudinal section and is formed in a manner corresponding to the guide groove 156, so that the second coupling member 164 is adapted to be inserted into the guide groove 156 in a direction transverse to a longitudinal axis 168 of the shaft 116 and is displaceable therein. The shaft 116 can be fixed to the adapter element 136 in the implantation disposition with the aid of a further securing device 187 which comprises two clamping screws 188 that are formed in a manner corresponding to the threaded borings 160. In the implantation disposition, the end faces 190 of the clamping screws 188 press against side faces 140 of the projection 166 which face away from the longitudinal axis 168 and are diametrically opposite.

A second coupling device 174 for connecting the shaft 116 and the adapter 134 comprises the second coupling member 164, the guide groove 156 and also the clamping screws 188 held in the threaded borings 160.

A second guidance device 182, which is constructed in the form of a linear guide means 184, comprises the projection 166 as well as the guide groove 156 which enables a translation of the shaft 116 relative to the adapter 134 in a direction transverse to the longitudinal axis 168. Consequently, an operating surgeon can match the implant part 110 individually to the anatomy of a patient, namely, in that the shaft 116 can be shifted relative to the adapter 134 in a desired manner in order to establish a displacement 192 between the longitudinal axes 132 and 168, and in that the adapter 134 can be rotated relative to the implant component 114 about the longitudinal axis 132 in the mounting disposition.

Figure 6:
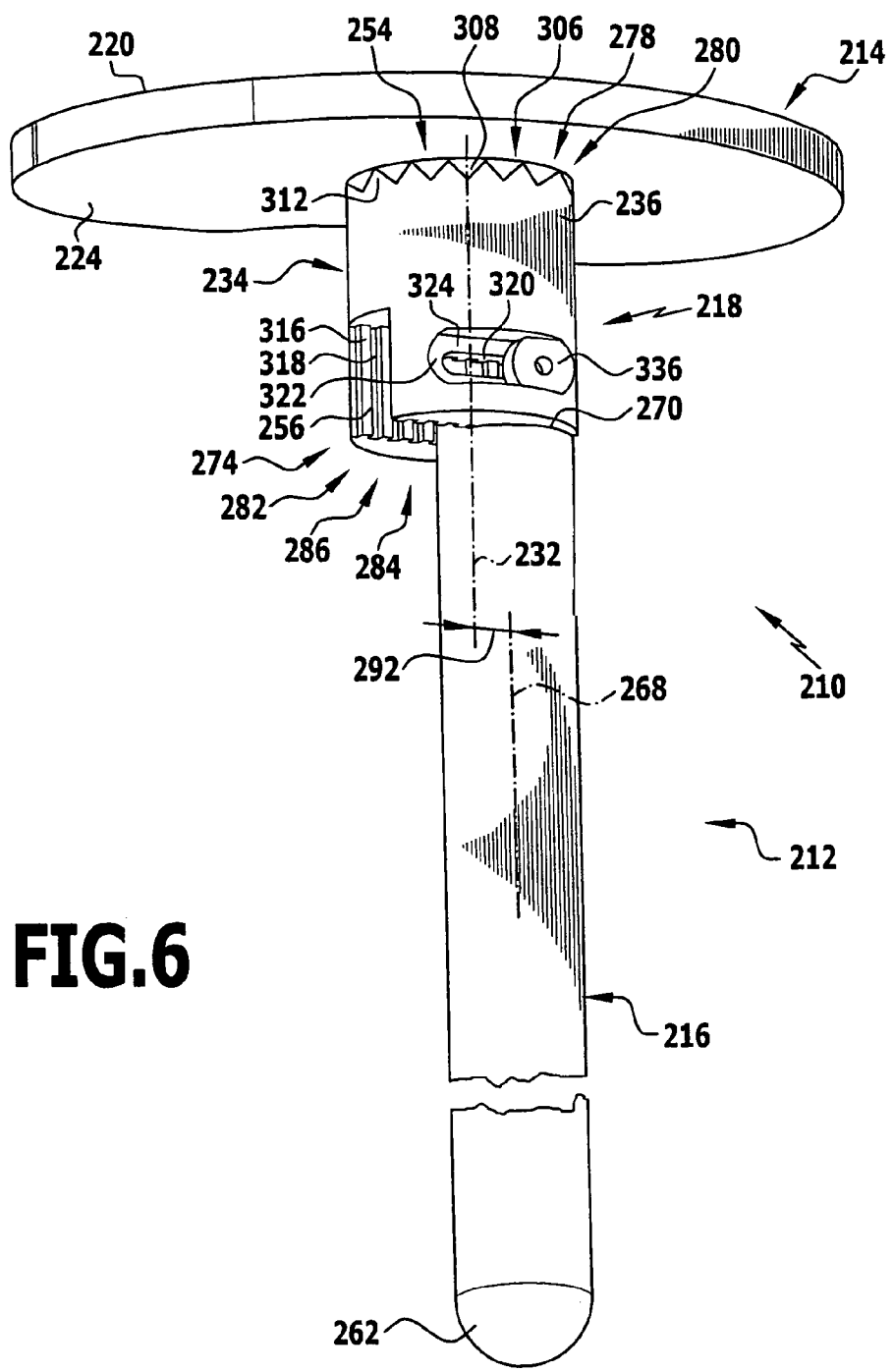
FIG. 6: a perspective view of a third exemplary embodiment of a modular implant part.
Figure 7:
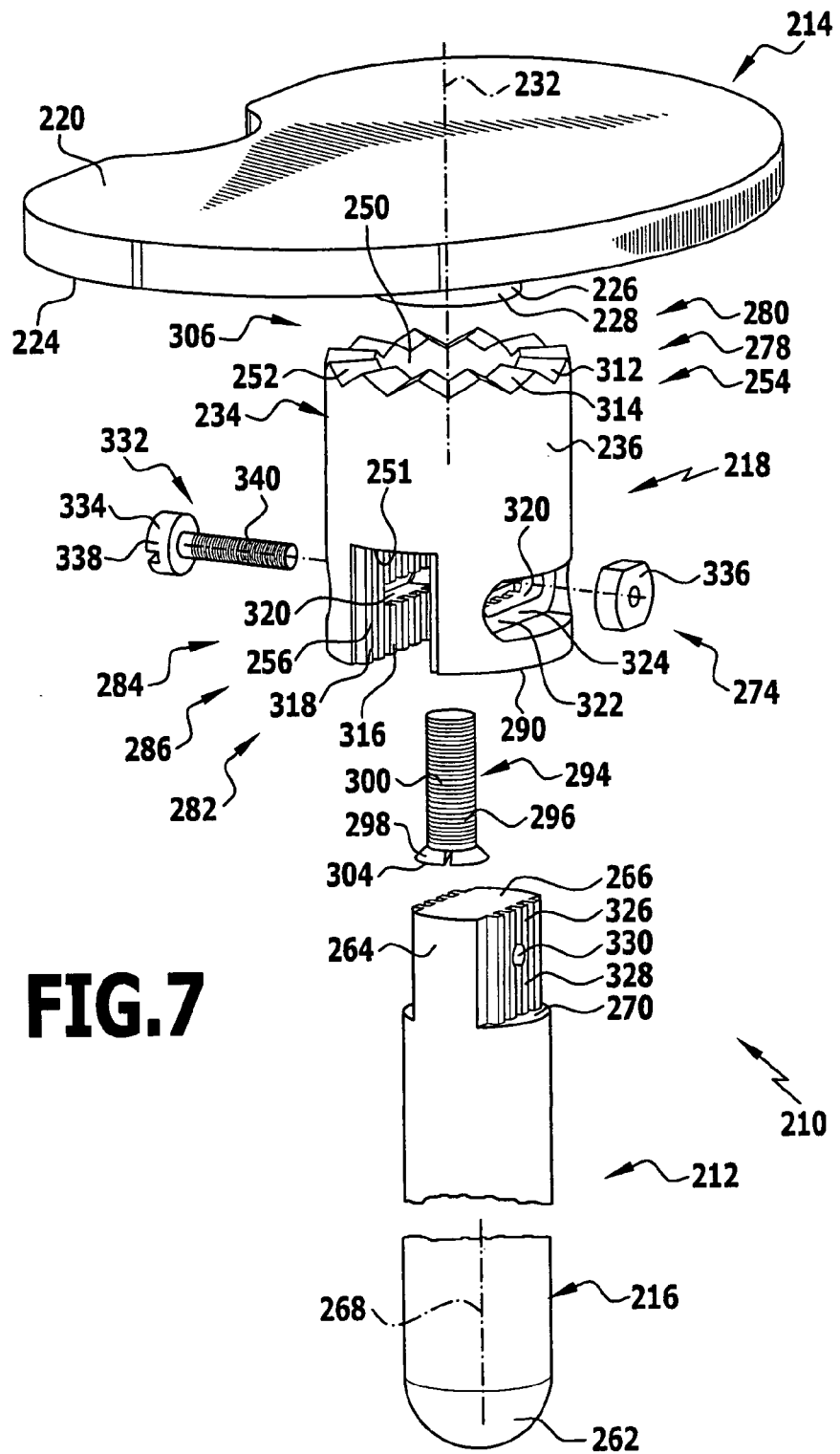
FIG. 7: an exploded view of the implant part depicted in FIG. 6.
Figure 8:
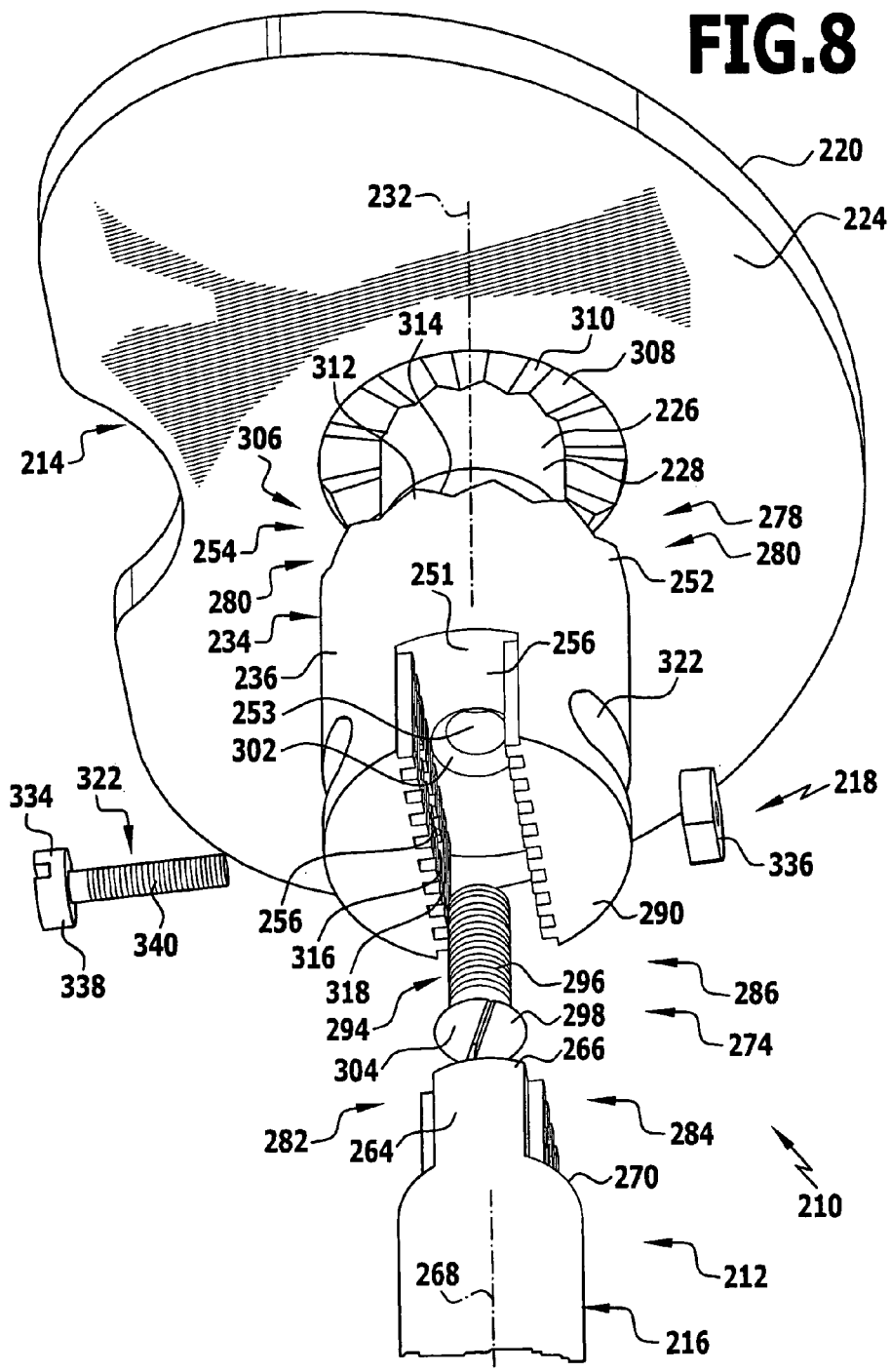
FIG. 8: an enlarged illustration of a detail of the implant part depicted in FIG. 7.

A further modular implant part in the form of a tibial part 212 that is provided with the general reference symbol 210 is illustrated in FIGS. 6 to 8. It comprises an implant component 214, a shaft 216 and a connecting device 218 for connecting the shaft 216 to the implant component 214.

The implant component 214 comprises a plate-like tibia plateau 220 which corresponds to the tibia plateau 20. For the sake of simplicity hereinafter, reference symbols having identical end digits are again used for the designation of parts of the implant part 210 which are identical or functionally similar to the parts of the implant part 10.

A first coupling member 226, namely, in the form of a stud-like projection 228, protrudes perpendicularly from a lower surface 224.

The connecting device 218 comprises an adapter 234 which can be connected to the implant component 214 on the one hand and to the shaft 216 on the other. The adapter element 236 is formed from a cylindrical base body and has a cylindrical blind hole 250 on the proximal side. The base 251 of the blind hole 250 is provided with a boring 253 which is oriented coaxially relative to a longitudinal axis 232 of the projection 228 in like manner to the blind hole 250.

Furthermore, a first coupling device 254 for connecting the adapter element 236 to the implant component 214 comprises a fastening element 294 in the form of a screw 296 having a head 298 and an externally threaded section 300. The externally threaded section 300 is dimensioned such that it can be pushed through the boring 253, whereby the latter has a countersunk, conical edge surface 302 facing in the distal direction so that a lower surface 304 of the head 298, which is in the form of a countersunk head, is flush with the base 251. Furthermore, the projection 228 is provided with a not illustrated blind hole boring which is coaxial to the longitudinal axis 232 so that the screw 296 can be screwed to the coupling member 226.

A positioning device 306 on the implant component 214 comprises a ring-like set of teeth 308 which surrounds the projection 228 in ring-like manner and has a plurality of teeth 310 which point in the distal direction. An edge surrounding the blind hole 250 and defining a proximal end 252 of the adapter element 236 is likewise in the form of a set of teeth 312, whereby the sets of teeth 308 and 312 are formed in mutually corresponding manner so that the teeth 310 of the set of teeth 308 can engage between the teeth 314 of the set of teeth 312 and vice versa. If the adapter element 236 is screwed to the implant component 214 by means of the screw 296, then the positioning device 306 comprising the sets of teeth 308 and 312 holds the adapter element 236 in a defined rotary position relative to the implant component 214. By loosening the screw 296, the adapter element 236 can be moved away from the implant component 214 in parallel with the longitudinal axis 232 to such an extent that the sets of teeth 308 and 312 disengage and the adapter element 236 can then be rotated about the longitudinal axis 232 relative to the implant component 214. For this purpose, a first guidance device 278 in the form of a rotary guide means 280 comprises the coupling member 226 and the blind hole 250.

A distal half of the adapter element 236 is provided with a slot-like guide groove 256 which is open in the distal direction and oriented transversely relative to the longitudinal axis 232. Inner side surfaces 316 of the guide groove 256 are provided with a respective set of teeth 318, whereby the teeth extend in parallel with the longitudinal axis 232 and have a cuboidal profile in each case. Perpendicularly to the guide groove 256 and likewise perpendicularly to the longitudinal axis 232, the side surfaces 316 are pierced by elongated holes 320, these extending in a direction which is oriented parallel to the guide groove 256. On an outer surface of the adapter element 236, there is provided a respective elongated depression 322, namely, in such a manner that there is formed a ring-shaped surface 324 of constant width which faces away from the longitudinal axis 232 and surrounds the elongated hole 320.

The shaft 216 is elongated and rod-shaped and has a hemispherical rounded-off end 262 which points in the distal direction. At the proximal end of the shaft, there is a second coupling member 264 in the form of a substantially cuboidal projection 266. Two side surfaces of the projection 266 facing transversely away from the longitudinal axis 268 of the shaft 216 form a part of the cylindrical outer surface of the shaft 216. Outer surfaces 226 formed substantially perpendicularly to the aforesaid side surfaces and likewise facing transversely away from the longitudinal axis 268 are provided with a respective set of teeth 328 which corresponds to the set of teeth 318 and which comprises elongated rows of teeth extending in parallel with the longitudinal axis 268. The construction and orientation of the sets of teeth 318 and 328 enables the shaft 216 to be moved into engagement with the adapter element 236 in different positions, namely, by a relative movement of the two parts towards one another in parallel with the longitudinal axis 268.

Due to the construction of the projection 266, two surfaces 270 are formed laterally thereof, these facing in the proximal direction and being oriented transversely relative to the longitudinal axis 268. Moreover, the projection 266 is provided with a transverse boring which is oriented perpendicularly to the outer surfaces 326 whilst the longitudinal axis thereof intersects the longitudinal axis 268. The boring together with a second fastening element 332 in the form of a cheese head screw 334 and a slide block 336 forms a securing device 286 for securing the shaft 216 to the adapter element 236 in the implantation disposition. The cheese head screw 334 has a head 338 and a threaded section 340 which protrudes perpendicularly away therefrom whilst the outer diameter thereof is matched to the width of the elongated holes 320 so that the threaded section 340 is displaceable in the elongated holes 320 transversely relative to the longitudinal axis 232. The slide block 336 has a threaded boring 342 and is formed in such a manner that two parallel, flattened sides thereof can likewise be slid along mutually facing inner surfaces of the depressions 322 in a plane extending perpendicularly to the longitudinal axis 232, without rotating, when the threaded section 340, which is formed in corresponding manner to the threaded boring 342, is screwed into the slide block 336. The transverse boring 330 has an inner diameter which is matched to the outer diameter of the threaded section 340 so that the threaded section 340 can be passed through the elongated holes 320 and the transverse boring 330 and can be screwed to the slide block 336 when the projection 266 is pushed into the guide groove 256.

An operating surgeon can also match the implant part 210 to the anatomy of a patient in a desired manner. For this purpose, the adapter element 236 is firstly fixed to the coupling member 226 of the implant component 214 with the aid of the screw 296 so that it is at least still possible to produce rotation about the longitudinal axis 232. When the guide groove 256 is oriented in the desired manner, the screw 296 can be tightened so that the sets of teeth 308 and 312 engage together and produce and also maintain a defined rotary position of the adapter element 236 and the implant component 214 relative to each other. In a next step, the second coupling member 264 of the shaft 216 is slid into the guide groove 256, namely, in such a manner that the longitudinal axis 268 and the longitudinal axis 232 exhibit the displacement 292 wanted by the operating surgeon. Due to the sets of teeth, the shaft 216 cannot of course be directly shifted in the guide groove 256 transversely relative to the longitudinal axis 268, but rather, it is initially disengaged from the adapter element 236 in order to then be transferred by a translatory movement in a direction transverse or substantially transverse to the longitudinal axis 268 into another translatory position defined by a second positioning device 344 comprising sets of teeth 318 and 328. In addition, the shaft 216 is adapted to be fixed immovably to the adapter element 236 in the implantation disposition with the aid of the securing device 286.

Figure 9:
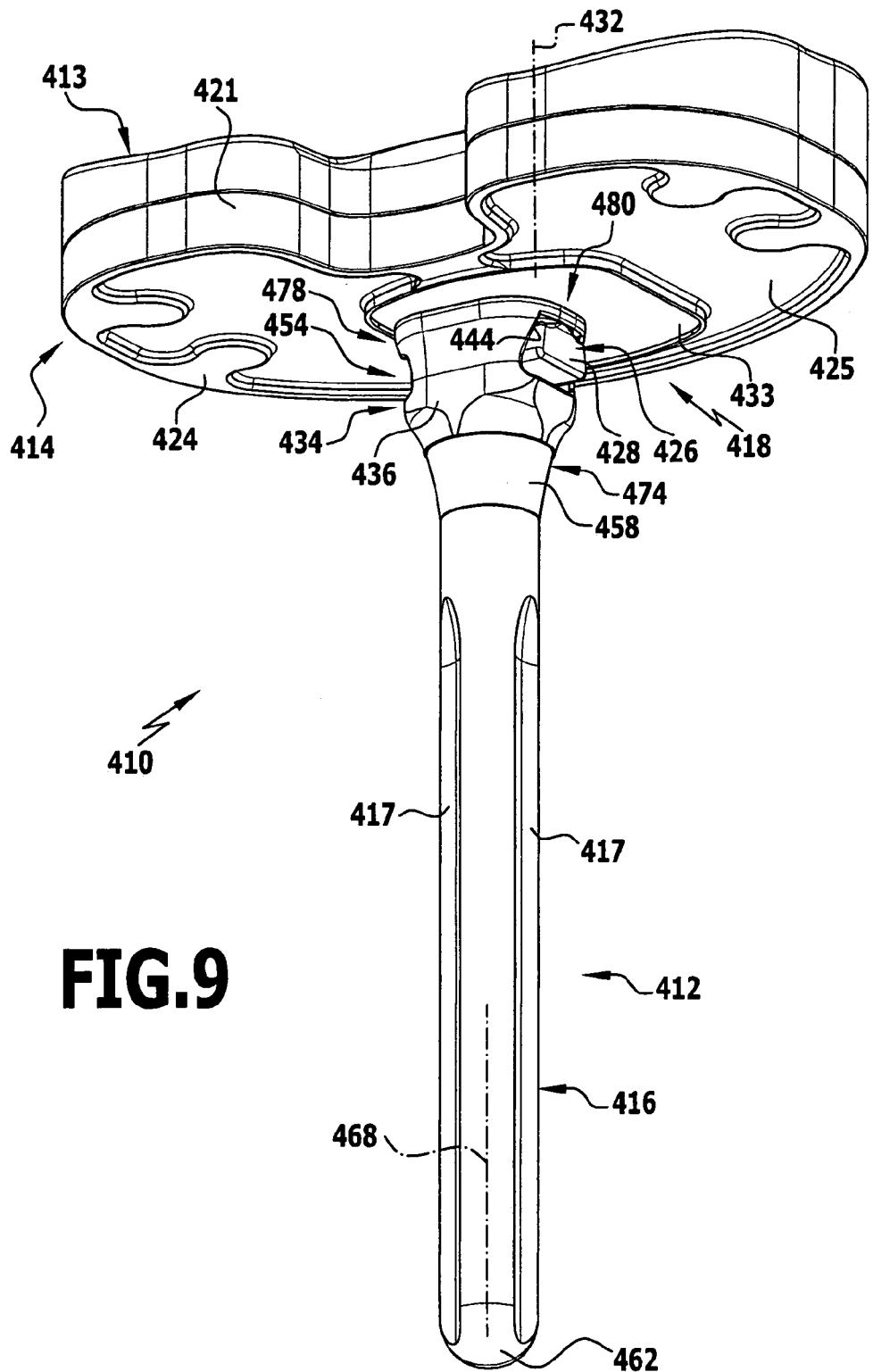
FIG. 9: a perspective view of a fourth exemplary embodiment of a modular implant part.
Figure 10:
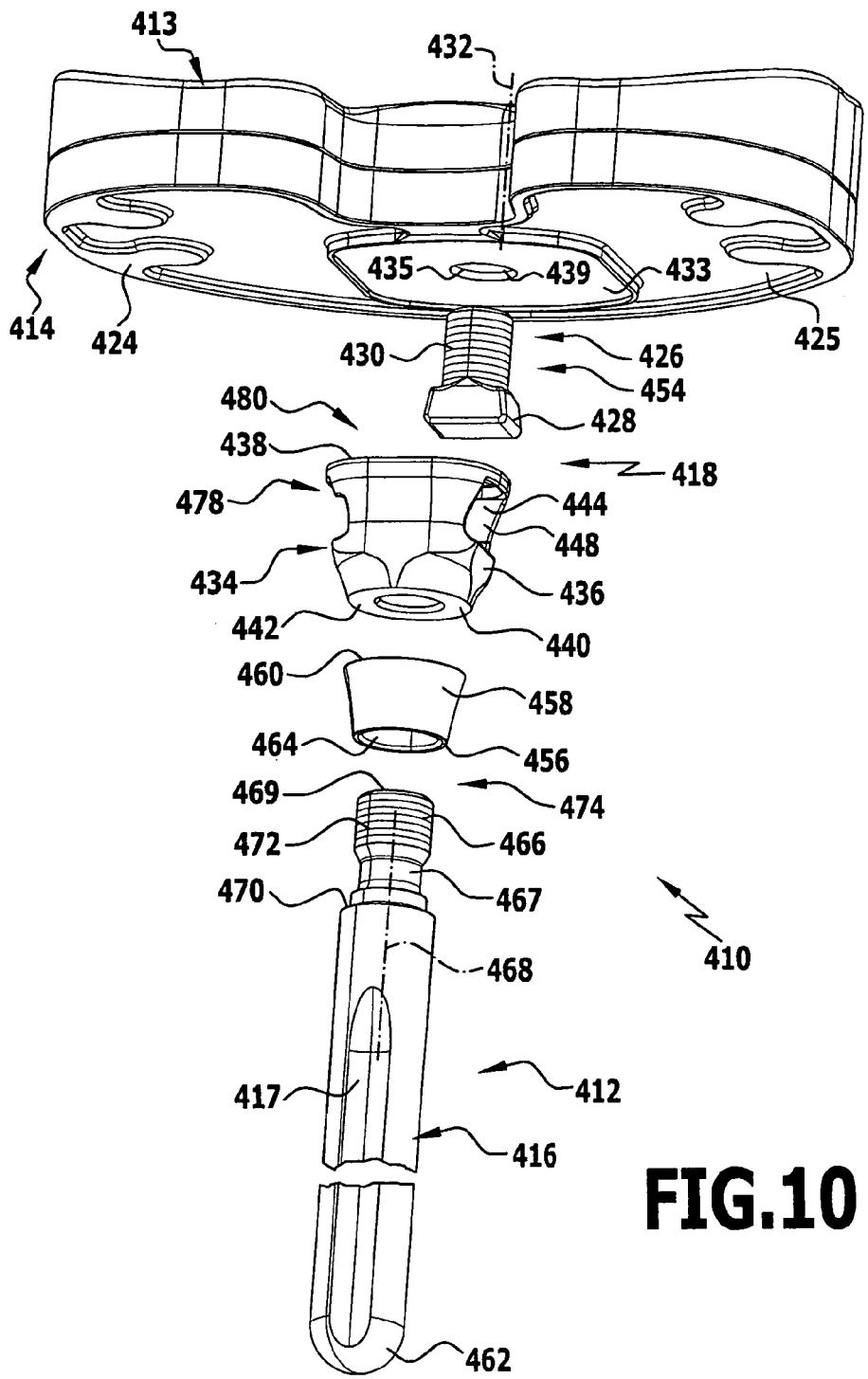
FIG. 10: an exploded view of the implant part depicted in FIG. 9 from below.
Figure 11:
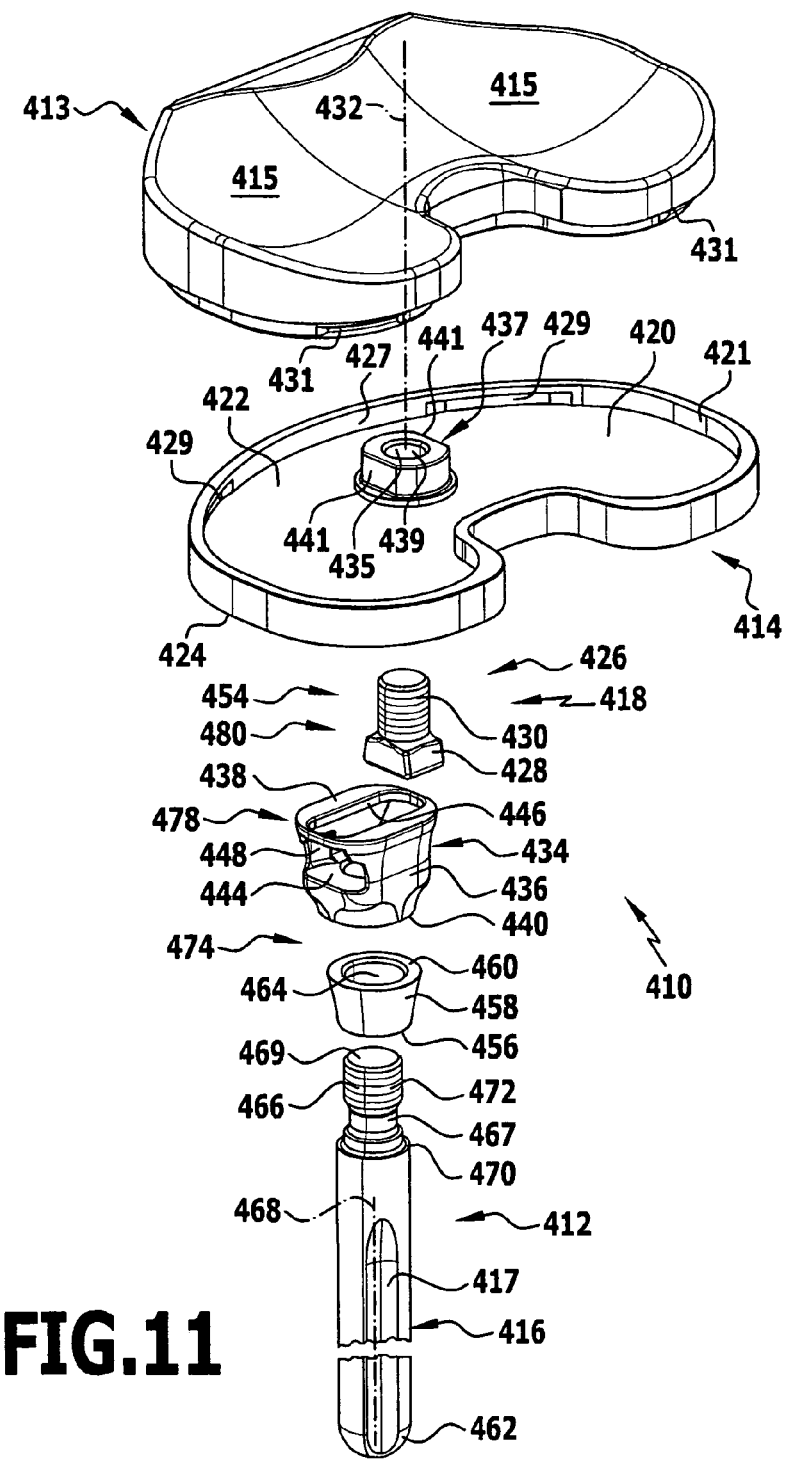
FIG. 11: an exploded view of the implant part depicted in FIG. 9 from above.

A further exemplary embodiment of a modular implant part that is provided with the general reference symbol 410 is illustrated in FIGS. 9 to 11. It is in the form of a tibial part 412 of a knee joint prosthesis which, furthermore, comprises a femoral part that is not illustrated in the Figures, as well as a meniscus part that is provided with the general reference symbol 413.

The implant part 410 comprises an implant component 414, an elongated substantially round rod-shaped shaft 416 which is provided with notch-like flattened regions or depressions 417 that extend in parallel with its longitudinal axis 468 over almost the entire length of the shaft and are arranged such as to be displaced relative to each other through an angle of 120° with respect to the longitudinal axis 468 although they could optionally be dispensed with. Furthermore, the implant part 410 comprises a connecting device 418 for connecting the implant component 414 to the shaft 416.

The implant component 414 comprises a plate that is substantially kidney-shaped in plan view and which forms a tibia plateau 420 the upper surface 422 of which is substantially flat in the exemplary embodiment illustrated in FIGS. 9 to 11. A lower surface 424 of the tibia plateau 420 is provided symmetrically with flat recesses 425 in order to save material and enable bone tissue to grow or to serve as an anchorage for bone cement, this thereby enabling the implant part 410 to be connected to the remaining part of the tibia of the patient in a particularly stable manner. Furthermore, the plate forming the tibia plateau 420 is provided with a peripheral edge 421 which is flush with the lower surface 424 and projects beyond the upper surface 422, namely, by about the same amount as the plate is thick. On an inner surface 427 of the edge 421, there are a plurality of recesses in the form of undercuts 429 which serve as latching members for cooperating with corresponding outwardly pointing projections 431 formed on the meniscus part 413 in order to enable the meniscus part 413 to be connected to the implant component 414 in latching manner. Extending away from the upper surface 422 of the meniscus part 413, there are sliding surfaces 415 that are matched to the curvature of the condyle of a not illustrated femoral part of the knee joint prosthesis. The meniscus part 413 and the implant component 414 are thus connectable such as to be immovable relative to each other.

Due to the special shape of the recesses 425, an approximately square surface region 433 is defined on the lower surface 424 through which there extends a boring 435 that defines a longitudinal axis 432. The boring serves for accommodating a cylindrical bolt section of a first coupling member 426 which is provided with an external thread 430 and has a head 428 having substantially cuboidal slightly conical exterior surfaces. The bolt section is of a length such that it is adapted to pass through the boring 435 and be screwed into a nut 437 having an internal thread corresponding to the external thread 430. In order to facilitate the task of screwing the first coupling member 426 into the nut 437, the latter has two parallel flattened portions 441 that face in opposite directions and run parallel to the longitudinal axis 432.

Moreover, the connecting device 418 includes an adapter 434 that comprises an adapter element 436 which is formed mirror-symmetrically relative to a mirror plane containing the longitudinal axis 432 and which has a flat upper surface 438 and a flat lower surface 440. Coaxially relative to the longitudinal axis 468, there is provided an internally threaded boring 442 which extends from the lower surface 440 up to a through opening 444 in the adapter 434 that runs transversely relative to the longitudinal axis 432. In side view, the through opening 444 has a profile which is matched to that of the head 428. In the upper surface 438 thereof, the adapter 434 is provided with a slot 446 the width of which corresponds to the diameter of the bolt section of the first coupling member 426 that is provided with the external thread 430. Furthermore, inner walls of the adapter 434 which bound the through opening 444 and are formed adjacent to a lateral opening therein are provided with symmetrically facing returns 448 that enable the externally threaded portion 430 of the first coupling member 426 to be initially introduced from the side thereof which can be seen on the left of the adapter 434 in FIG. 11. The head 428 can thus be introduced into the through opening 444 which defines a guidance means therefor. The first coupling member 426 is displaceable transversely relative to the longitudinal axis 432 in the through opening 444 defining a linear guide means.

Due to the fact that the first coupling member 426 is adapted to be fixed to the tibia plateau 420 through the boring 435 in conjunction with the nut 437 in a defined manner, it is thus possible to adjust the adapter 434 relative to the tibia plateau 420 in such a manner that the adapter, the upper surface 438 of which is resting on the surface region 433, is displaceable transversely relative to the longitudinal axis 432 when the implant part 410 has adopted its mounting disposition, i.e. when the nut 437 is not as yet clamping the first coupling member 426 against the tibia plateau 420 with maximum force. Moreover, rotation of the adapter 434 about the longitudinal axis 432 in the mounting disposition is also possible, whether or not any "offset" has been set. Here, "offset" means a lateral displacement between the longitudinal axis 432 and the longitudinal axis or axis of symmetry 468 of the internally threaded boring 442.

The shaft 416 has a hemispherical rounded-off distal end 462. The opposite end thereof carries a coupling element 472 in the form of a threaded bolt section 466. Adjoining the latter on the distal side, there is a section 467 of reduced internal diameter which however, is stepped up again in the distal direction, whereby this widened section has a smaller outer diameter than the threaded bolt section 466. As a consequence thereof, a ring-shaped surface 470 facing in the proximal direction is formed, i.e. in the direction of the tibia plateau 420. This serves as a stop surface for a ring-like end face 456 of a collar sleeve 458 that has a conically tapering outer contour in the distal direction whilst the proximal end thereof likewise defines a ring-shaped surface 460 which rests against the lower surface 440. The collar sleeve 458 is provided with a cylindrical boring 464 that is aligned coaxially with the longitudinal axis 468 whilst the internal diameter thereof is selected in such a manner that the collar sleeve 458 is adapted to be pushed over the proximal end of the shaft 416 until the end face 456 rests against the ring-shaped surface 470. In addition, the height of the collar sleeve 458 parallel to the longitudinal axis 468 is smaller than the spacing between a proximal end face 469 of the threaded bolt section 466 running transverse to the longitudinal axis 468 and the ring-shaped surface 470. Thus, the threaded bolt section 466 protrudes beyond the collar sleeve 458, this thereby enabling the threaded bolt section 466 to be threaded into the internally threaded boring 442 of the adapter 434 for the purposes of connecting the shaft 416 to the adapter 434.

The collar sleeve 458 makes it possible for different shafts 416, which can differ in shape and length in particular, to be connected to the adapter 434. In particular, it provides optimal support for the shaft 416 relative to the adapter 434, namely, independently of manufacturing tolerances occurring during the production of the shaft 416, in particular, at its proximal end comprising the threaded bolt section 466.

Thus, in toto, the connecting device 418 is formed in such a manner that the shaft 416 is connectable to the implant component 414, whereby, in a mounting disposition in which the nut 437 and the first coupling member 426 are not yet firmly screwed onto one another, the shaft 416 is adapted to be moved into different translatory positions by displacement of the adapter 434 in a direction transverse to the longitudinal axis 468, i.e. by a translatory movement, and, in addition, it is adapted to be fixed immovably to the implant component 414 in one of the arbitrarily different translatory positions by tightening the nut 437 and the first coupling member 426. In particular, the adapter is formed in such a manner that stepless adjustment of differing translatory positions is possible in the mounting disposition.

As previously mentioned, in the mounting disposition, the shaft 416 is rotatable about a rotational axis defined by the longitudinal axis 432 into different rotary positions relative to the implant component 414 by virtue of the special construction of the adapter 434 and, in the implantation disposition, it is adapted to be fixed to the implant component 414 in one of the different rotary positions due to the special construction of the connecting device. In the implantation disposition, the adapter 434 is adapted to be fixed both to the implant component 414 and to the shaft 416 in the manner described.

The adapter element 436 is formed symmetrically, namely, symmetrically relative to a plane of symmetry which contains the longitudinal axis 468 and is oriented at half the angle to planes defined by lateral inner surfaces of the through opening 444. The implant component 414 comprises the first coupling member 426 which is in engagement in force-locking and/or shape-locking manner with the adapter 434 in the implantation disposition. The first coupling member 426 is in the form of a coupling projection when it is held on the implant component 414 by the nut 437.

A first coupling device 454 for immovably fixing the adapter 434 to the implant component 414 is formed by the through opening 444 in combination with the slot 446, the first coupling member 426 and also the boring 435 and the nut 437. The first coupling device 454 comprises first coupling elements in the form of the through opening 444 as well as the first coupling member 426 the head 428 of which engages with the through opening 444 in the implantation disposition. The implant component 414 thus comprises the first coupling element in the form of the head 428 and the adapter 434, a further first coupling element in the form of the through opening 444. Thus, the first of the coupling elements comprises a recess in the form of the through opening 444 and the other coupling element comprises a projection in the form of the head 428 which enters the through opening 444 in the implantation disposition.

Furthermore, the connecting device 418 comprises a second coupling device 474 for immovably fixing the adapter 434 to the shaft 416 in the implantation disposition. The second coupling device 474 comprises two second coupling elements, namely, the internally threaded boring 442 and the coupling element 472 which are in engagement in the implantation disposition, namely, by a screw action, whereby the shaft 416 comprises the coupling element 472 in the form of the threaded bolt section 466 and the adapter 434 the internally threaded boring 442. The adapter 434 and the first and second coupling elements comprised thereby in the form of the through opening 444 and the internally threaded boring 442 are formed in one piece.

Furthermore, the connecting device 418 comprises a first guidance device 478 for guiding a movement of the adapter 434 and the implant component 414 relative to each other in the mounting disposition in the manner described above. Furthermore, the first guidance device 478 comprises a rotary guide means 480 which enables the adapter 434 to be rotated about the longitudinal axis 432 relative to the implant component 414. Furthermore, the first guidance device 478 comprises the first coupling member 426.

Figure 12:
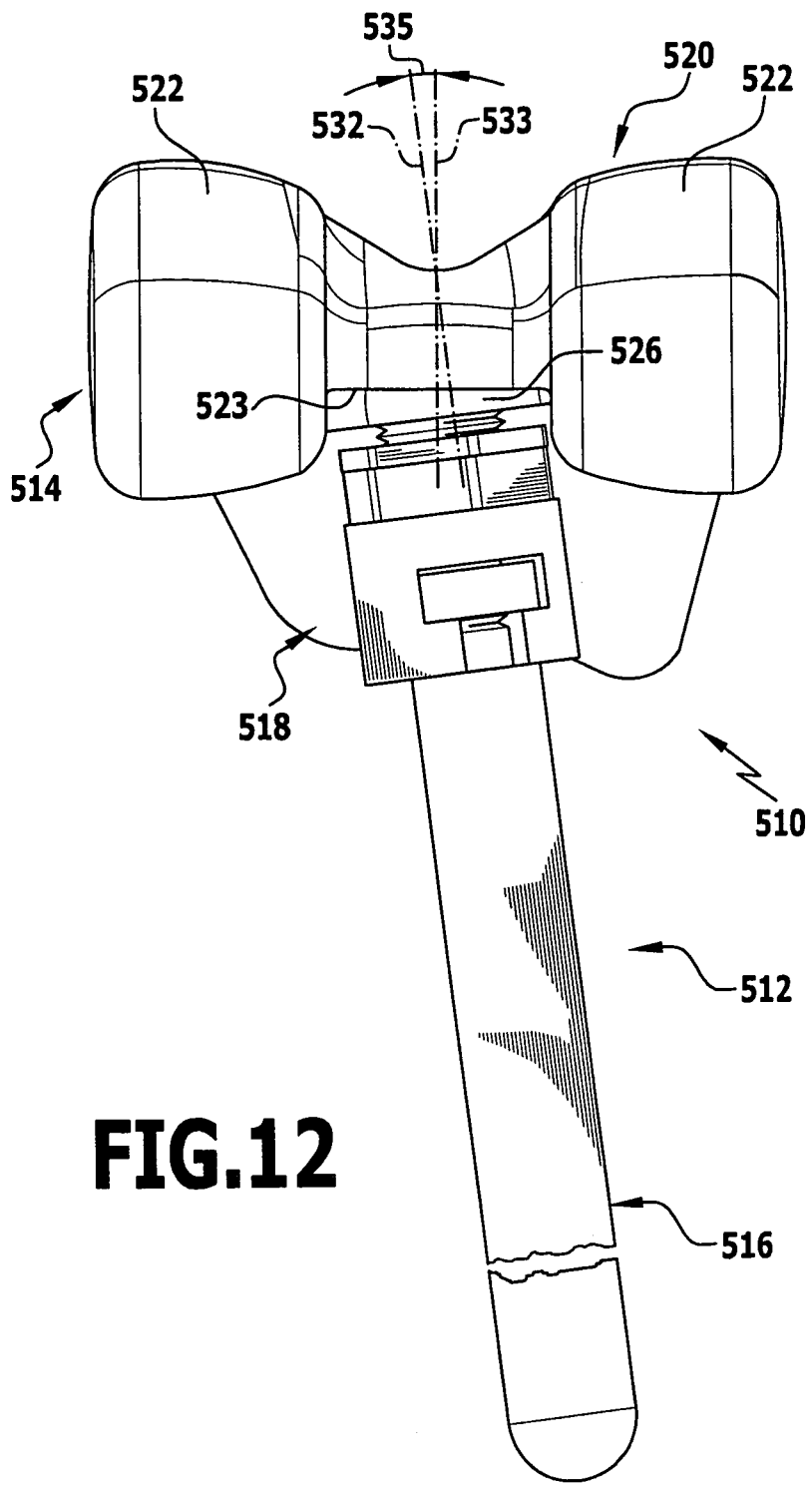
FIG. 12: a side view of a fifth exemplary embodiment of a modular implant part.

Self-evidently, the shafts 16, 116, 216 and 416 described above can be fixed not only to an implant component comprising a tibia plateau, but also to an implant part 510 forming a femoral part 512 having a condyle body 520 comprising two artificial femoral condyles 522 which define articulation surfaces that are in contact with a not illustrated meniscus part of the knee joint prosthesis. An implant part of this type is illustrated exemplarily in FIG. 12. The shaft 516 can be connected by means of a connecting device 418 to the condyle body 520. For this purpose, the latter includes a coupling member 526 which can be formed in identical manner to the coupling members 26, 126 and 226. Accordingly, the connecting device 518 can also be formed in identical manner to the connecting devices 18, 118 and 218 described above. Then, in corresponding manner, the shaft 516 is also formed identically to the shafts 16, 116 and 216 so that reference can be made to the above explanations for a detailed description thereof.

Optionally, the coupling member 526 can be inclined at an angle 535, which can lie in a range from 0° to 15°, relative to a femur plateau 523 which is defined by a side of a projection-like body connecting the two femoral condyles 522. Self-evidently, the respective longitudinal axes 32, 132 and 232 of the coupling members 26, 126 and 226 can be inclined relative to the surface-normals of the lower surfaces 24, 124 and 224 of the respective implant components 14, 114 and 214 in similar manner.

Common to all the modular implant parts described above, is that per se, both the implant component and the adapter element as well as the respective shaft can be formed at least mirror-symmetrically, and partly rotationally symmetrically.

Optionally, a plurality of shafts of different lengths can be provided for connecting to the respective implant component so that an implant part in the form of a set is in each case at the disposal of an operating surgeon, whereby each set comprises an implant component, an adapter and one or more shafts. All of the implant parts described above are made of a body-compatible material, preferably of a body-compatible metal.

The invention claimed is:

1. A modular implant part for replacing a part of a natural knee joint comprising:
    an implant component comprising a plate-like tibia plateau having an upper surface and a lower surface,
    a shaft, and
    a connecting device comprising a single adapter for connecting the shaft to said implant component, the adapter is adapted to be fixed to the implant component on the one hand and the shaft on the other hand,
    said shaft defining a longitudinal axis and extending away from said implant component,
    in a mounting disposition the adapter and the implant component are temporarily connected while still allowing a relative movement therebetween such that the adapter is: (i) adapted to be moved into different translatory positions with respect to the lower surface of the tibia plateau by a translatory movement in a direction transverse or substantially transverse to said longitudinal axis; and (ii) the adapter is rotatable about an axis of rotation into different rotary positions with respect to the lower surface of the tibia plateau, the axis of rotation running parallel or substantially parallel to the longitudinal axis of the shaft, and
    in an implantation disposition, the adapter is adapted to be immovably fixed to the implant component in one of the different translatory positions and one of the different rotary positions,
    wherein:
        a first coupling member is provided which couples the implant component and adapter together and is in engagement in at least one of a force-locking and a shape-locking manner with the adapter in the implantation disposition,
        the connecting device comprises a first guidance device for guiding a movement of the adapter and the implant component relative to each other in the mounting disposition,
        the first guidance device comprises a linear guide means comprised of at least one guide groove formed on the adapter, and
        a head of the first coupling member is guided in the guide groove in linear movable manner in the mounting disposition.

2. A modular implant part in accordance with claim 1, wherein the connecting device is formed in such a manner that it is possible for different translatory positions to be set in a step-less manner in the mounting disposition.

3. A modular implant part in accordance with claim 1, wherein the shaft is adapted to be fixed immovably to the implant component by the connecting device in one of the different rotary positions in the implantation disposition.

4. A modular implant part in accordance with claim 1, wherein the connecting device is formed in such a manner that it is possible to set differing rotary positions in a step-less manner in the mounting disposition.

5. A modular implant part in accordance with claim 1, wherein the adapter comprises an adapter element which is formed symmetrically or substantially symmetrically.

6. A modular implant part in accordance with claim 1, wherein the first coupling member is constructed in the form of a bolt.

7. A modular implant part in accordance with claim 1, wherein the connecting device comprises a first coupling device for immovably fixing the adapter to the implant component in the implantation disposition.

8. A modular implant part in accordance with claim 1, wherein:
    at least two first coupling elements are provided which are in engagement in the implantation disposition, and
    the implant component comprises one of the at least two first coupling elements and wherein the adapter comprises another one of the at least two first coupling elements.

9. A modular implant part in accordance with claim 8, wherein one of the at least two first coupling elements comprises an internally threaded section and another of the at least two first coupling elements comprises a corresponding externally threaded section.

10. A modular implant part in accordance with claim 8, wherein one of the at least two first coupling elements comprises a recess and another of the at least two first coupling elements comprises a projection which enters the recess in the implantation disposition.

11. A modular implant part in accordance with claim 10, wherein the recess is in the form of a groove and the projection is in the form of a screw, whereby at least one part of the screw enters the groove in the implantation disposition.

12. A modular implant part in accordance with claim 8, wherein the adapter and the first coupling element comprised thereby are in one piece.

13. A modular implant part in accordance with claim 1, wherein the connecting device comprises a second coupling device for immovably fixing the adapter to the shaft in the implantation disposition.

14. A modular implant part in accordance with claim 1, wherein:
    at least two second coupling elements are provided which are in engagement in the implantation disposition,
    the shaft comprises one of the at least two second coupling elements, and
    the adapter comprises another one of the at least two second coupling elements.

15. A modular implant part in accordance with claim 14, wherein the at least two second coupling elements are in engagement with each other in the implantation disposition.

16. A modular implant part in accordance with claim 14, wherein one of the at least two second coupling elements is constructed in the form of a coupling projection.

17. A modular implant part in accordance with claim 14, wherein one of the at least two second coupling elements comprises an internally threaded section and another one of the at least two second coupling elements comprises a corresponding externally threaded section.

18. A modular implant part in accordance with claims 14, wherein one of the at least two second coupling elements comprises a recess and another one of the at least two second coupling elements comprises a projection which enters the recess in the implantation disposition.

19. A modular implant part in accordance with claim 18, wherein the recess is in the form of a groove and the projection is in the form of a screw, whereby at least one part of the screw enters the groove in the implantation disposition.

20. A modular implant part in accordance with claim 14, wherein the adapter and the second coupling element comprised thereby are formed in one piece.

21. A modular implant part in accordance with claim 1, wherein the first guidance device comprises a rotary guide means.

22. A modular implant part in accordance with claim 1, wherein a free end of the shaft is rounded off.

23. A modular implant part in accordance with claim 1, wherein a plurality of shafts of different lengths are provided.

24. A modular implant part in accordance with claims 1, wherein the implant part forms a tibial part of a knee joint prosthesis.

25. A modular implant part in accordance with claim 1, wherein the connecting device is formed in such a manner that the shaft is fixable in the translatory position and in the rotary position independently of each other.

26. A knee joint prosthesis comprising a first implant part, a second implant part and a third implant part, said first implant part being in the form of a femoral part, said second implant part being in the form of a tibial part and said third implant part being in the form of a meniscus part,
said second implant part is a modular implant part,
said modular implant part comprising:
an implant component comprising a plate-like tibia plateau having an upper surface and a lower surface,
a shaft, and
a connecting device comprising a single adapter for connecting the shaft to the implant component, the adapter is adapted to be fixed to the implant component on the one hand and the shaft on the other hand,
said shaft defining a longitudinal axis and extending away from the implant component,
wherein:
in a mounting disposition the adapter and the implant component are temporarily connected while still allowing a relative movement therebetween such that the adapter is:
(i) adapted to be moved into different translatory positions with respect to the lower surface of the tibia plateau by a translatory movement in a direction transverse or substantially transverse to said longitudinal axis; and (ii) the adapter is rotatable about an axis of rotation into different rotary positions with respect to the lower surface of the tibia plateau, the axis of rotation running parallel or substantially parallel to the longitudinal axis of the shaft; and
in an implantation disposition, the adapter is adapted to be fixed immovably to the implant component in one of the different translatory positions and one of the different rotary positions,
a first coupling member is provided which couples the implant component and adapter together and is in engagement in at least one of a force-locking and a shape-locking manner with the adapter in the implantation disposition,
the connecting device comprises a first guidance device for guiding a movement of the adapter and the implant component relative to each other in the mounting disposition,
the first guidance device comprises a linear guide means comprised of at least one guide groove formed on the adapter, and
a head of the first coupling member is guided in the guide groove in linear movable manner in the mounting disposition.

27. A knee joint prosthesis in accordance with claim 26, wherein the connecting device is formed in such a manner that the shaft is fixable in the translatory position and in the rotary position independently of each other.

* * * * *